(12) United States Patent
Collins

(10) Patent No.: US 8,110,000 B2
(45) Date of Patent: Feb. 7, 2012

(54) LIGAMENT RECONSTRUCTION SYSTEM

(76) Inventor: Evan D. Collins, Houston, TX (US)

( * ) Notice: Subject to any disclaimer, the term of this patent is extended or adjusted under 35 U.S.C. 154(b) by 963 days.

(21) Appl. No.: 12/043,832

(22) Filed: Mar. 6, 2008

(65) Prior Publication Data

US 2009/0228017 A1 Sep. 10, 2009

(51) Int. Cl.
*A61F 2/08* (2006.01)
*A61B 17/58* (2006.01)

(52) U.S. Cl. ........................ 623/13.11; 606/96

(58) Field of Classification Search ................ 606/86 R, 606/96, 98; 623/13.11–13.19
See application file for complete search history.

(56) References Cited

U.S. PATENT DOCUMENTS

| | | |
|---|---|---|
| 4,712,542 A | 12/1987 | Daniel et al. |
| 5,520,693 A | 5/1996 | McGuire et al. |
| 5,562,668 A | 10/1996 | Johnson |
| 6,325,804 B1 | 12/2001 | Wenstrom, Jr. et al. |
| 6,725,082 B2 | 4/2004 | Sati et al. |
| 6,878,150 B1 | 4/2005 | McGuire et al. |
| 7,575,578 B2 * | 8/2009 | Wetzler et al. .................. 606/96 |

* cited by examiner

*Primary Examiner* — Bruce E Snow
(74) *Attorney, Agent, or Firm* — Egbert Law Offices PLLC

(57) ABSTRACT

A system for ligament reconstruction includes placing a first jig having a first plurality of drill guide holes on a first bone of the joint, forming two intersecting holes in the first bone using the first plurality of drill guide holes, placing a second jig having a second plurality of drill guide holes on a second bone of the joint, forming a tunnel and a first branch hole and a second branch hole in the second bone using the second plurality of drill guide holes, placing a tendon having sutured ends through the two intersecting holes, extending the sutured ends through the tunnel and through the first and second branch holes so that the first and second ends of the tendon are positioned within the tunnel, and affixing the tendon within the tunnel. The apparatus of this system has specially formed jigs placed over bones.

15 Claims, 4 Drawing Sheets

LIGAMENT RECONSTRUCTION SYSTEM

CROSS-REFERENCE TO RELATED APPLICATIONS

Not applicable.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

BACKGROUND OF THE INVENTION

1. Field of the Invention

The present invention relates to ligament reconstruction. More particularly, the present invention the relates to systems of ligament reconstruction of a joint using a tendon graft. More particularly still, the present invention the relates to systems for ligament reconstruction of an elbow.

2. Description of Related Art Including Information Disclosed Under 37 CFR 1.97 and 37 CFR 1.98.

The human body is comprised of many joints including the ankle, the knee, the shoulder, and the elbow. At each of these joints, there are two bones connected by a ligament. Over time, a ligament can become stretched or torn because of over-stressed movement or an injury. When this happens ligament reconstruction is needed.

Ligament reconstruction typically reestablishes joint stability through a bone-tendon connection. A tendon is taken from another part of the body and is woven through bone tunnels that have been drilled in each of the bones of the joint. The tendon is appropriately tensioned between the two bones of the joint, and then the tendons are usually secured to the bones of the joint.

Surgical methods for reconstructing ligaments of a joint have existed for years. For example, a method for reconstruction of a ligament of an elbow, called "Tommy John surgery", has been a common procedure since its inception in 1974. "Tommy John surgery" is most commonly performed on pitchers in the sport of baseball. Because pitching overhand is a particularly stressful motion, pitching at high speeds puts a substantial strain on a pitcher's elbow joint and is commonly injurious. Injuries resulting from the stressful motion of pitching can range from a sprain to a tear of the ligament of the elbow. Regardless of the severity of the injury, a "Tommy John surgery" is usually needed to restore a pitchers arm to full velocity.

Tommy John surgery is much like other methods of ligament reconstruction for other joints. Ligament reconstruction has historically entailed individual assessment of a patient's anatomy so as to determine the correct placement for a graphed tendon. The individual assessment also determines the location of the bone tunnels utilized for a reconstruction surgery. In every patient, bone tunnels through which the ligaments are threaded are created with every effort to ensure the best placement, equal size, and symmetry. Likewise, appropriate tendon length and tension is also individually assessed and applied. The process of ligament reconstruction is recreated with each individual patient and each surgeon, with inevitable variations due more to human error rather than any error attributable to a device or apparatus. Moreover, there is usually no standard navigation device or uniform system for a ligament reconstruction procedure. Even slight variations in tunnel location, size or symmetry of the tunnels, as well as tendon length and tension, can impact the outcome and recovery of the patient. Thus, there is a need for a more uniform system and procedure for ligament reconstruction, especially for that of the elbow.

In the past, various patents have issued relating to ligament reconstruction. For example, U.S. Pat. No. 6,725,082, issued on Apr. 20, 2005 to Sati et al., discloses a method of obtaining data indicative of a location for ligament graft placement. Medical image data representative of a bone is provided. Position data indicative of an intraoperative position of each of a plurality of points associated with a surface of the bone is obtained. The medical image data and the position data are related to one another mathematically to obtain transformed data indicative of the location for ligament graft placement. This patent also relates to a system for obtaining data indicative of a location for ligament graft placement. The system includes a computer configured to receive medical image data representative of a bone and a pointer or ultrasound device configured to determine position data indicative of an intraoperative position of one or more points associated with a surface of the bone.

U.S. Pat. No. 4,712,542, issued on Dec. 15, 1987 to Daniel et al., describes a method and instrument for skeletal-referenced isometric positioning and tensioning of a ligament graft, particularly during knee surgery involving the anterior cruciate and the posterior cruciate ligaments. The graft is extended from one fixation site and attached to a sled slidably carried by a frame which is skeletally mounted to the other fixation site. A thumb nut and lead screw assembly on the skeletally-fixed frame is operative to compress a spring in the sled and move the sled in a direction effective to tension the graft. Isometry is achieved when the relative positions of the frame and sled indicate constant graft tension and displacement through the entire range of passive knee flexion. The sled can be fixed relative to the frame for evaluation of joint laxity.

U.S. Pat. No. 6,325,804, issued on Dec. 4, 2001 to Wenstrom Jr. et al., discloses a method for performing an anterior cruciate ligament repair procedure wherein a bone plug attached to a section of tendon or ligament is fixed in a bone tunnel. The method utilizes an adhesive to secure the bone block in the bone tunnel.

U.S. Pat. No. 5,562,668, issued on Oct. 8, 1996 to Johnson, discloses a screw tensioning device for holding at least one end of a ligament graft. The device has a thimble which locates in the mouth of a hole drilled through bone, a nut captively seated in the thimble, and an anchorage element with a screw-threaded stud which can engage the nut. Different forms of anchorage elements are provided for different grafts, but each is adapted to securely hold one end of a ligament graft. The anchorage element with a ligament attached is drawn through the hole from the opposite side to the thimble until the stud engages the nut. The nut is then turned by a tool until the required tension is achieved.

U.S. Pat. No. 6,878,150 issued on Apr. 12, 2005 to McGuire et al., discloses a method for precisely forming bone tunnels in a cruciate ligament reconstruction of the knee. The method generally includes the steps of drilling a hole in one of the bones, using a femoral guide to determine the placement of the second tunnel, and drilling the second tunnel according to the position of the femoral guide. The femoral guide is cannulated.

U.S. Pat. No. 5,520,693, issued on May 28, 1996 to McGuire et al., discloses a device for forming bone tunnels in cruciate ligament reconstruction of the knee. The device has an elongate body that includes a cylindrical member and an arcuate surface extending from the cylindrical member. A lumen located in the body receives a guide wire. The lumen extends for the length of the cylindrical member through an opening formed on the arcuate surface so as to allow the guide wire to protrude from the elongate body. This allows the guide wire to contact the bone surface. A tongue located on the body is used to engage the edge of bone surface whereby the guide wire protruding from the body contacts the bone surface.

It is an object of the present invention to provide a system for ligament reconstruction of the joints of the human body.

It is another object of the present invention to provide a system for standardizing the ligament reconstruction of a joint.

It is another object of the present invention to minimize variations in ligament reconstruction from patient to patient.

It is still a another object of the present invention to improve the efficiency of ligament reconstruction.

It is another object of the present invention to provide a ligament reconstruction system that reduces the assessment time for performing ligament reconstruction.

It is another object of the present invention to provide a system for ligament reconstruction with jigs anatomically contoured to the cortical topography of the bones of a joint.

It is still another object of the present invention to provide a system for ligament reconstruction that precisely measures tendon graft length.

It is another object of the present invention to provide a system for ligament reconstruction that provisionally tests a reconstruction for tension and stability.

It is another object of the present invention to provide a system for ligament reconstruction of the ulna and humerus of the elbow.

It is yet another object of the present invention to provide a system for ligament reconstruction that creates uniform hole dimensions in the ulna of an elbow.

It is still another object of the present invention to provide a system for ligament reconstruction that precisely locates and forms tunnels and holes in the humerus of an elbow.

These and other objects and advantages of the present invention will become apparent from a reading of the attached specification and appended claims.

BRIEF SUMMARY OF THE INVENTION

The present invention is a method for reconstructing a ligament of a joint. The method includes placing a first jig having a first plurality of drill guide holes on a first bone of the joint, forming two intersecting holes in the first bone using the first plurality of drill guide holes of the first jig, placing a second jig having a second plurality of drill guide holes on a second bone of the joint, forming a tunnel and a first branch hole and a second branch hole in the second bone using the second plurality of drill guide holes, placing a tendon through a passageway formed by the two intersecting holes in the first bone such that a first end and a second end of the tendon extend outwardly of the passageway, attaching first and second sutures to the first and second ends of the tendon, respectively, extending the first and second sutures through the tunnel and respectively through the first and second branch holes such that the first and second ends of the tendon are positioned within the tunnel and the first and second sutures extend outwardly respectively of the first and second branch holes, and affixing the first and second ends of the tendon within the tunnel. The joint contemplated by the present invention is an elbow. The first bone of the elbow is the ulna, and the second bone of the elbow is the humerus.

The method of the present invention further includes securing the first jig to the first bone prior to the step of forming two intersecting holes, securing the second jig to the second bone prior to the step of forming the tunnel and the first branch hole and the second branch hole, removing the first jig from the first bone after the step of forming two intersecting holes, and removing the second jig from the second bone after the step of affixing the tendon. The method of the present invention also further includes adjusting a length of the tendon by securing the first suture to the second jig, clamping the second suture to a handle affixed to the second jig, adjusting the first bone and the second bone of the joint to a desired position, and adjusting the handle so as to fix the length of the tendon.

The step of securing the first jig includes inserting a first securing pin through a pin guide hole into the first bone adjacent to a joint line, and inserting a second securing pin through a cannulated handle removably affixed to the first body into the first bone. The step of clamping includes pulling a second suture in through a slot in a the handle, the slot being centered at a proximal end of the tunnel.

The step of forming two intersecting holes includes attaching drill sleeves to each of the plurality of drill guide holes, inserting a drill bit into each of the drill sleeves, drilling the intersecting holes with the drill bit in the first bone, and reaming the intersecting holes. The drill sleeves have axes intersecting a short distance from the first jig inside the first bone.

The step of forming a tunnel includes attaching a first drill guide to a first drill guide hole of the second plurality of drill guide holes, inserting a drill bit into the first drill guide, and drilling the tunnel to a desired depth. The step of forming the first and second branch holes includes attaching a second drill guide to a second drill guide hole of the second plurality of drill guide holes, inserting the drill bit into the second drill guide, drilling the first branch hole, removing the second drill guide from the second drill guide hole, attaching a third drill guide to a third drill guide hole of the second plurality of drill guide holes, inserting the drill bit into the third drill guide, drilling second branch hole, and removing the third drill guide from the third drill guide hole. The first and second branch holes have a smaller diameter than a diameter of the tunnel.

The step of affixing the first and second ends of the tendon can include tying the first and second sutures together. The step of affixing the first and second ends of the tendon can also include placing locking plugs in the tunnel through the first and second branch holes.

The present invention is also an apparatus for ligament reconstruction. The apparatus has a first jig and a second jig. The first jig has a body formed so as to fit over a first bone. The second jig is arranged in spaced relation to the first jig and has a body formed so as to fit over a second bone of a joint. A plurality of openings and at least one pin guide hole are formed in the body of the first jig. A handle is placed on the body of the first jig. The plurality of openings are located on the body of the first jig so as to have axes intersecting a desired distance from one side of the first jig. The second jig has a first drill guide hole, a second drill guide hole, a third drill guide hole, and at least one fixing hole formed in the body of the second jig. The second and third drill guide holes have axes intersecting at a desired distance from one side of the second jig. These axes also intersect a longitudinal axis of the first dill guide hole. The second jig also has a second handle affixed to the body thereof.

In particular, the first jig has a surface formed so as to fit over a portion of an ulna of an elbow. The second jig has a surface formed so as to fit over a portion of a humerus of an elbow. The plurality of openings have a diameter of between 10 to 15 millimeters. The first drill guide hole has a diameter of approximately 8 millimeters. The second and third drill guide holes have a diameter smaller than the diameter of the first drill guide hole.

DETAILED DESCRIPTION OF THE INVENTION

Figure 1:
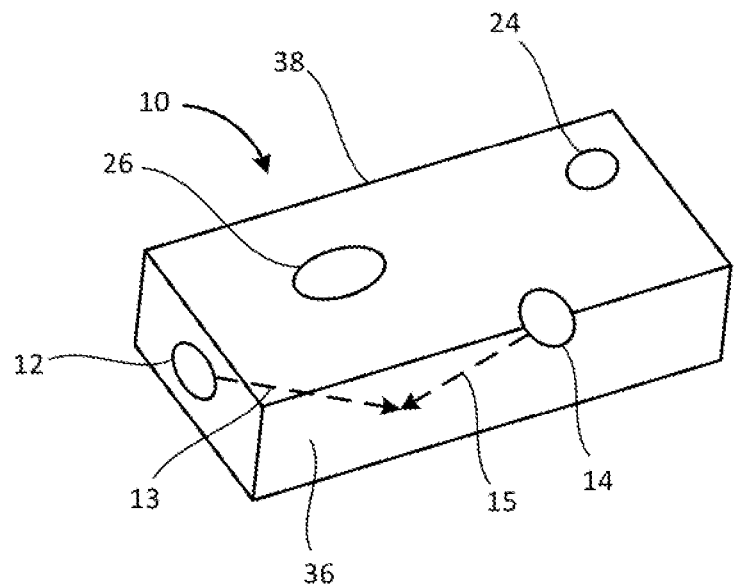
FIG. 1 is a schematic view of the first jig of the apparatus of the present invention.

The ligament reconstruction system of the present invention involves an apparatus and method for using the apparatus. Referring to FIG. 1, there is shown the first jig 10 of the apparatus of the present invention. The first jig 10 is generally rectangular in shape. The first jig 10 has a plurality of openings formed on the surface 36 of the body 38 thereof. The first hole 12 of the plurality of openings is formed on the wall of the body 38 furthest from the joint line. The second hole 14 of the plurality of openings is formed through the body 38 of the first jig 10 where one of the side walls meets the top of the body 38. The first hole 12 has an axis 13, and the second hole 14 has an axis 15. Both axes 13 and 15 are shown as dotted lines in FIG. 1. As can be seen, the axis 13 of the first hole 12 and the axis 15 of the second hole 14 intersect at a short distance from the body 38 of the first jig 10. There is a pin guide hole 24 for inserting a pin therethrough. The pin is inserted through the pin guide hole 24 so as to secure the first jig 10 to one bone of a joint. The surface 26 of the first jig 10 also has a threaded hole 26 for a handle. The handle (not shown) is threadedly attached to the threaded hole 26 for positioning the first jig 10 on the bone of the joint.

As can also be seen, the first jig 10 has a surface 36 that is contoured to fit over one bone of a joint. In the preferred embodiment of the present invention, the first jig 10 is contoured to fit over the ulna of an elbow. The wall furthest from the joint line has a surface contoured to fit over the ulna of an elbow. In medial collateral ligament reconstruction, the first jig 10 is contoured to fit over the medial side of the ulna. In lateral collateral ligament reconstruction, the first jig 10 is contoured to fit over the lateral cortex of the ulna. The present invention contemplates using the first jig 10 on any one of two bones of any joint.

Figure 2:
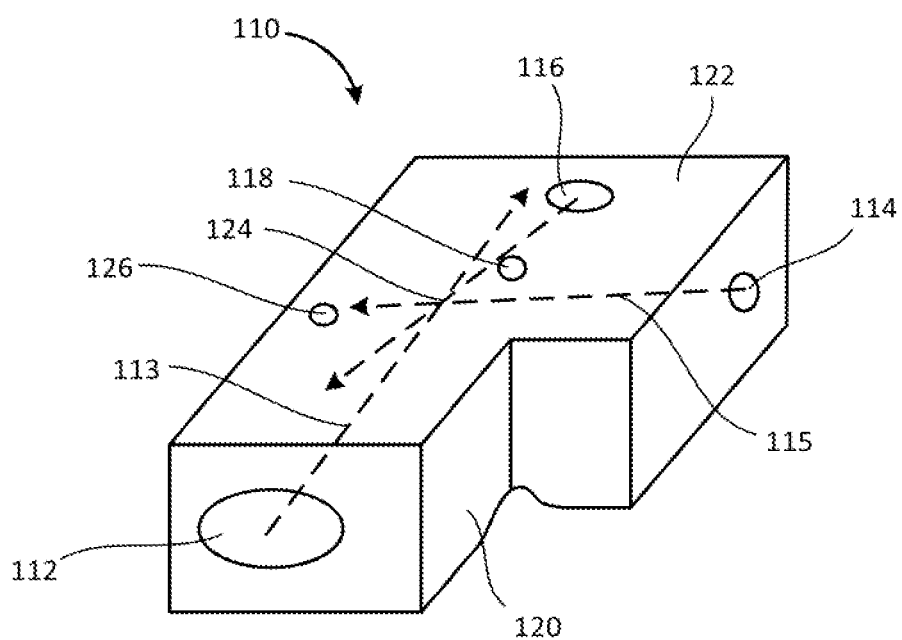
FIG. 2 is a schematic view of the second jig of the apparatus of the present invention.

Referring to FIG. 2, there is shown the second jig 110 of the apparatus of the present invention. The first drill guide hole 112 is located on the wall of the second jig 110 closest to the joint. A second drill guide hole 114 is located on another wall of this surface 120 of the jig 110, and a third drill guide hole 116 is located on the top of the second jig 110. The first drill guide hole 112 has a longitudinal axis 113 that runs parallel with the length of the second jig 110. The second drill guide hole 114 has an axis 115 that intersects the longitudinal axis 113 of the first drill guide hole 112. The third drill guide hole 116 has an axis 117 that intersects the longitudinal axis 113 of the first drill guide hole 112. In the preferred embodiment of the second jig 110 of the present invention, the longitudinal axis 113 of the first drill guide hole 112 intersects the axis 115 of the second drill guide hole 114 and the axis 117 of the third drill guide hole 116 at the axes intersections point 124. At the intersection point 124 of the axes, all axes of the drill guide holes 112, 114, and 116 intersect. As can be seen, the axes 113, 115, and 117 are shown in FIG. 2 as dotted lines.

A first fixing hole 118 and a second fixing hole 126 are formed on the body 122 of the second jig 110. The first fixing hole 118 and the second fixing hole 126 are used to place pins therethrough for securing the second jig 110 to the bone of the joint. In particular, the pins secure the second jig 110 to the humerus of an elbow.

Referring still to FIG. 2, the second jig 110 has a body 122 with a surface 120 contoured to fit over the bone of a joint. As can be seen, the second jig 110 is generally rectangular in shape. In the preferred embodiment of the present invention, the second jig 110 has a surface 120 that is contoured to fit over the humerus of an elbow. In medial collateral ligament reconstruction, the second jig 110 is contoured to fit over the cortex of the medial epicondyle of the humerus of an elbow. In lateral collateral ligament reconstruction, the second jig 110 is contoured to fit over the humeral lateral epicondyle of the humerus. The present invention contemplates using the second jig 110 on any one of two bones of any joint.

Using the first jig 10 and the second jig 110, holes are drilled in the bones of a joint. Using the preferred embodiment of the present invention, holes are formed in the ulna of an elbow with the first jig 10 and formed in the humerus of the elbow with second jig 110. The tendon graft 4 is pulled through the holes in these bones by the sutures 7 and 8 affixed to the ends 5 and 6 of the tendon graft 4.

Figure 3:
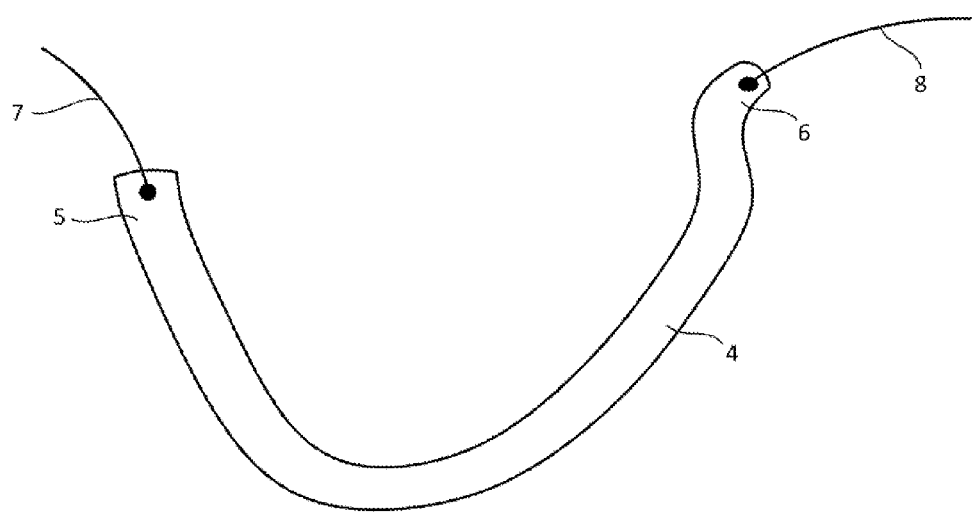
FIG. 3 is a schematic view of a tendon graft as used in the present invention.

Referring to FIG. 3, there is shown a tendon graft 4 having a first end 5 and a second end 6. Attached to the first end 5 of the tendon graft 4 is a first suture 7. Likewise, attached to the second end 6 of the tendon graft 4 is a second suture 8. The tendon graft 4 is used in the present invention to connect the two bones of a joint when a ligament has become sprained or torn. The tendon graft 4 is placed in the holes drilled in the ulna using the first jig 10 and in the holes drilled in the humerus using the second jig 110. Once placed in the holes of the ulna and humerus, the tendon graft 4 is tensioned and then affixed to the joint so as to operate as a ligament reconstruction.

Figure 4:
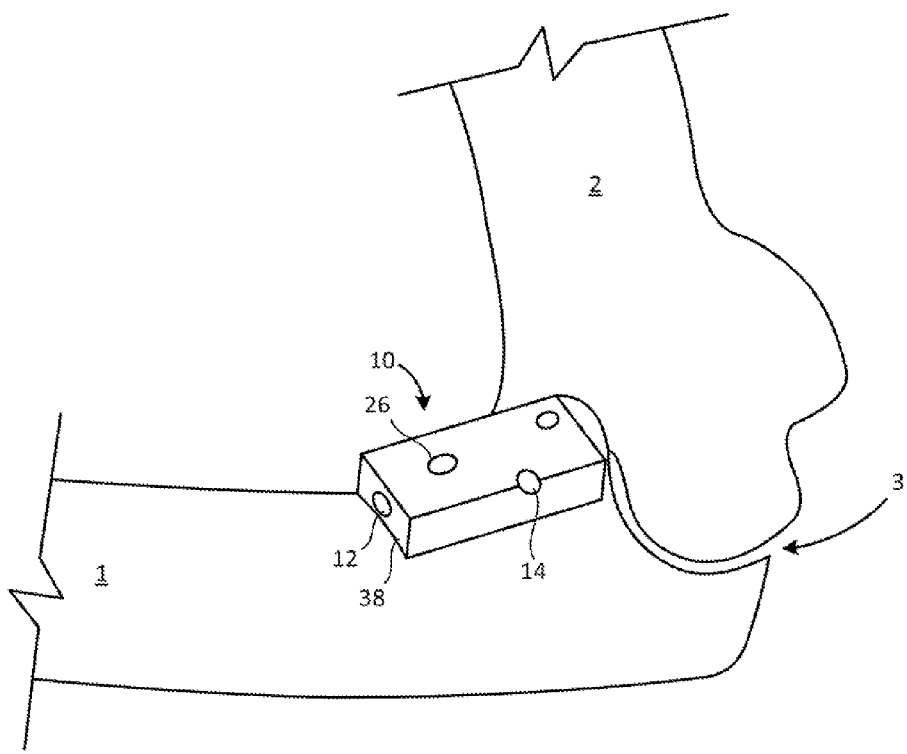
FIG. 4 is a perspective view of the first jig of the present invention as used on the ulna of an elbow.

Referring to FIG. 4, there is shown the first jig 10 of the present invention as placed on the ulna 1 at the elbow 3. As can be seen for medial collateral ligament reconstruction, the underside of the first jig 10 is formed so as to fit atop the medial side of the ulna 1 centered on the sublime tubercle.

The first jig 10 is positioned in place on the sublime tubercle on the ulna 1 by using a handle (not shown). The first hole 12 and the second hole 14 of the plurality of openings are formed in the body 38 of the first jig 10 so as to have axes to intersect within the ulna 1. In this way, a drill can be placed through the first hole 12 and the second hole 14 of the first jig 10 so that intersecting holes are formed in the ulna 1. These holes that can be drilled in the ulna 1 intersect so as to form a passageway (not shown) within the ulna 1. As can be seen in FIG. 4, the first jig 10 is placed adjacent to the joint line of the elbow 3.

Figure 5:
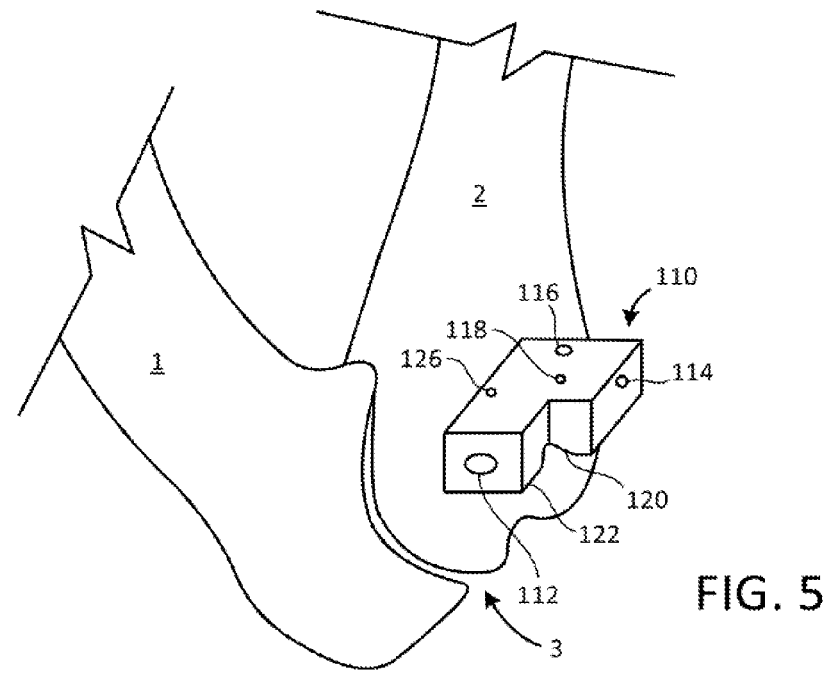
FIG. 5 is a perspective view of the second jig as used on the humerus of the elbow.

Referring to FIG. 5, there is shown a perspective view of the second jig 110 as placed on the humerus 2 of an elbow 3. The surface 120 of the body 122 of the second jig 110 can be seen as specially fitting over the humerus 2 of the elbow 3. As can be seen for the medial collateral ligament reconstruction shown in FIG. 5, the underside of the second jig 110 is formed so as to fit over the cortex of the medial epicondyle of the humerus 2. Although not shown in FIG. 5, the first drill guide hole 112, the second drill guide hole 114, and the third drill guide hole 116 have axes intersecting like those shown in FIG. 2. As can be seen in FIG. 5, the diameter of the first drill guide hole 112 is large enough to accommodate both ends of the tendon graft 4. Also, the diameter of the first drill guide hole 112 is larger than the diameters of each of the second drill guide hole 114 and the third drill guide hole 116. The first drill guide hole 112 is formed so as to be oval-shaped. The fixing hole 118 and the second fixing hole 126 are strategically placed so as to avoid intersecting the axes of the drill guide holes.

Figure 6:
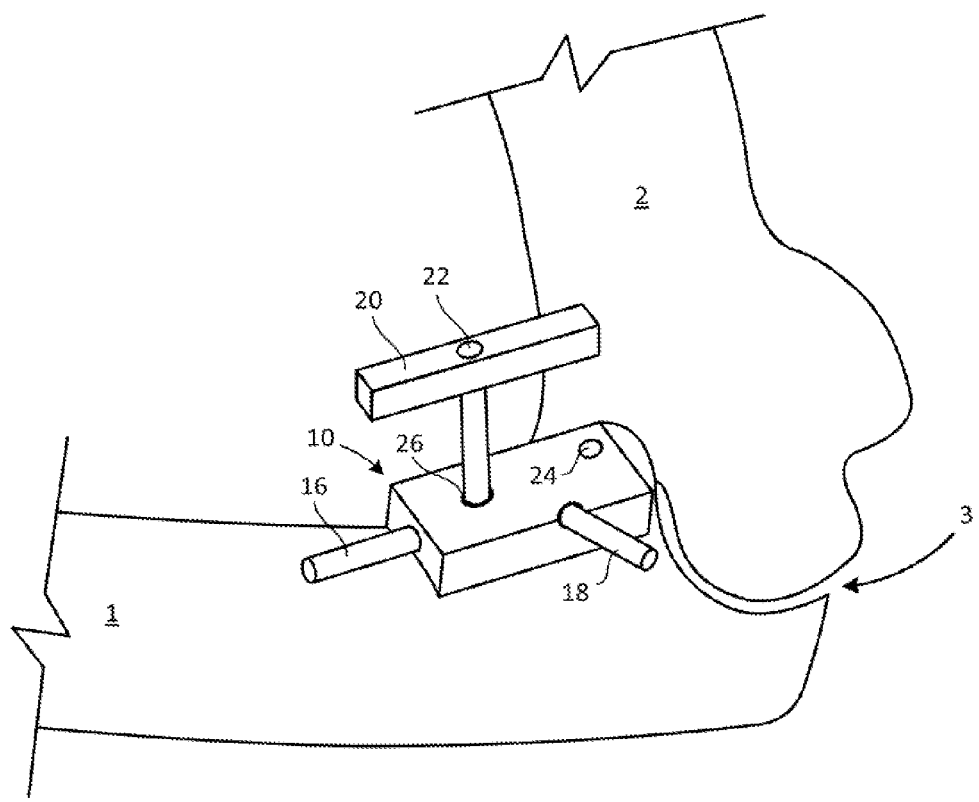
FIG. 6 shows a perspective view of the first jig mounted on the ulna of an elbow, with a first jig having drill sleeves and a handle mounted thereto.

Referring to FIG. 6, there is shown the first jig 10 as placed on the ulna 1 with drill sleeves and a handle attached thereto. The first drill sleeve 16 is attached to the first hole 12 of the plurality of openings. The axis of the first drill sleeve 16 is aligned with the axis 13 of the first hole 12. A second drill sleeve 18 is attached to the second hole 14 of the plurality of openings. The axis of the second drill sleeve 18 is aligned with the axis 15 of the second hole 14. A handle 20 is attached to the threaded hole 26 atop the first jig 10. The handle 20 is used to position the first jig 10 upon the ulna 1. The handle 20 has a cannulated center 22 wherein a pin is placed for securing the first jig 10 to the ulna 1. More particularly, a pin is inserted through the cannulated center and through the threaded hole 26 of the first jig 10 so as to penetrate the ulna 1 and affix the jig 10 to the ulna 1 during ligament reconstruction. A pin guide hole 24 is strategically placed on the first jig 10 for placing another pin therethrough so as to further secure the first jig 10 to the ulna 1. The pin placed through the pin guide hole 24 is closer to the joint line of the elbow 3 than is the pin placed through the cannulated center 22 of the handle 20.

After the first jig 10 is secured to the ulna 1, the handle 20 can be removed from the hole 26 of the first jig 10. A step drill having a drill bit is used to drill holes in the ulna 1 for ligament reconstruction. In the preferred embodiment of the present invention, the holes are drilled in the medial side of the ulna 1 for medial collateral ligament reconstruction. A drill bit is first placed into the first drill sleeve 16 and used to drill a hole into the ulna 1. The drill sleeve 16 ensures that the drill bit enters the ulna at a certain angle and drills consistently within the ulna 1. The drill bit is then placed in the second drill sleeve 18 to drill another hole so as to create two intersecting holes in the ulna 1. The second drilling sleeve 18 acts to support the drill bit and guide it into the ulna 1 so as to form a uniform hole like that made by drilling through the first drill sleeve 16. The holes that are drilled by drilling through the first drill sleeve 16 and second drill sleeve 18 intersect within the ulna 1 so as to create a passageway for extending a tendon graft therethrough. The first drill sleeve 16 is connected to the first jig 10 at the first hole 12. Likewise, second drill sleeve 18 is connected to the first jig 10 at the second hole 14.

One unique aspect of the present invention is that reamers are passed through the first and second drill guides, 16 and 18, and into the ulna 1 so as to further create a uniformly dimensioned passageway therein. The reamers are special, flexible reamers that eliminate any sharp edges between the two intersecting holes. This creates a better passageway for passing the tendon graft 4 therethrough.

Once the passageway is formed in the ulna 1 by drilling through the first drill sleeve 16 and the second drill sleeve 18, the first drill sleeve 16 and second drill sleeve 18 can be removed from the first jig 10. At this point, the pins securing the first jig 10 to the ulna can also be removed so as to remove the first jig 10 from the ulna 1.

Figure 7:
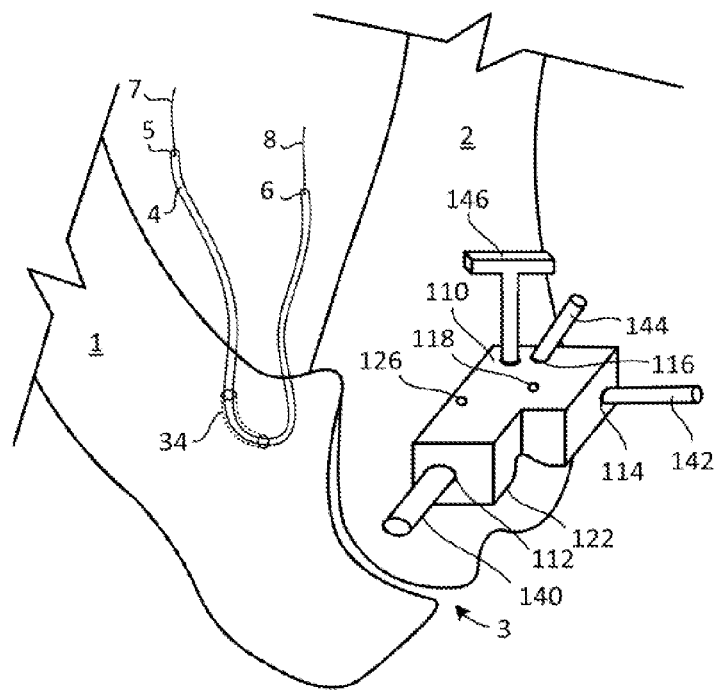
FIG. 7 is a perspective view of the second jig mounted on the humerus of an elbow, with the second jig having drill guides attached thereto. Also show is the tendon inserted into the tunnel of the ulna that is formed by using the first jig, with the first jig removed from the ulna.

Referring to FIG. 7, there is shown the tendon graft 4 placed through the passageway 34 of the ulna 1. After removing the first jig 10 from the ulna 1, the tendon graft 4 is extended through the passageway 34 created by the two intersecting holes. In particular, the first end 5 is pulled through the passageway 34 in the ulna 1. More particularly, the first end 5 of the tendon 4 is pulled through the passageway 34 by first pulling the first suture 7 attached to the first end 5 of the tendon 4 through the passageway 34. After pulling the tendon 4 through the passageway 34 both the first end 5 and the second end 6 should extend outwardly of the passageway 34. Likewise, the first suture 7 should extend from the first 5 of the tendon 4, and the second suture 8 should extend from the second end 6 of the tendon 4.

Referring again to FIG. 7, there is shown the second jig 110 of the present invention mounted on the humerus 2 of the elbow 3 with drill guides 140, 142, and 144 mounted thereto. The first drill guide 140 is attached to the body 122 of the second jig 110 at the first drill guide hole 112. The second drill guide 142 is attached to the body 122 of the second jig 110 at the second drill guide hole 114. The third drill guide 144 is attached to the body 122 of the second jig 110 at the third drill guide hole 116. The first drill guide 140 has an axis aligned with the longitudinal axis 113 of the first drill guide hole 112. The second drill guide 142 has an axis aligned with the axis 115 of the second drill guide hole 114. The third drill guide 144 has an axis aligned with the axis 117 of the third drill guide hole 116. Pins are placed through the first fixing hole 118 and the second hole 126 so as to secure the second jig 110 to the humerus 2 of the elbow 3. Pins are placed through the first fixing hole 118 and the second fixing hole 126 so as to not intersect any of the axes of the drill guides.

A drill bit is used to drill a tunnel hole through the humerus 2. The tunnel hole is formed by inserting the drill bit through the first drill guide 140 and drilling to a depth of approximately 15 millimeters. It is important to note that the tunnel hole is oval-shaped. After a tunnel hole is drilled in the humerus 2, the first drill guide 140 is removed from the first drill guide hole 112. Specifically machined side-cutting burrs are used to create a symmetrical oval shape for the tunnel hole. The diameter of the oval-shaped tunnel hole is approximately 8 millimeters.

Next, a first branch hole is drilled by inserting a drill bit into the second drill guide 142 and drilling into the humerus 2. The drill bit is inserted into the humerus 2 until the first branch hole intersects the tunnel hole. The drill bit is then inserted into the third drill guide 144 and drilled into the humerus 2. A drill bit drills a second branch hole to a depth in the humerus 2 where the second branch hole intersects the tunnel hole. The branch holes are formed at the proximal end of the tunnel hole. The first and second branch holes can also be referred to as proximal holes.

Once all the holes are drilled in the humerus 2, the first suture 7 attached to the first end 5 of the tendon graft 4 is pulled through the tunnel hole so that first end 5 of the tendon graft 4 resides in the tunnel hole and the first suture 7 extends outwardly of the first branch hole. The first suture is provisionally secured around the pin in the first fixing hole 118. The second end 6 of the tendon graft 4 is then provisionally placed in a slot of the handle 146 of the second jig 110. The handle 146 is centered at the proximal end of the oval tunnel. This is strategically done so as to simulate the desired length of the tendon needed within the tunnel but without having to place the second end 6 of the tendon graft 4 within the tunnel. It is desirable to simulate this length outside of the tunnel so that the tendon graft 4 can be cut to a desired length before placing the tendon graft 4 within the tunnel hole. Thus, the second end 6 of the tendon graft 4 is clamped to the slot in the handle 146. The ulna 1 and humerus 2 of the elbow 3 are adjusted so as to be in a correct position. The tendon graft 4 is then tensioned according to this desired position of the ulna 1 and humerus 2 of the elbow. Once tensioned, any excess length is cut from the tendon 4. The second end 6 of the tendon graft 4 is then unclamped from the handle 146 and passed through the tunnel hole in the humerus 2 so that the second end 6 of the tendon 4 remains within the tunnel hole and the second suture 8 extends out of the second branch hole. The jig is then removed from the medial epicondyle of the humerus 2.

Figure 8:
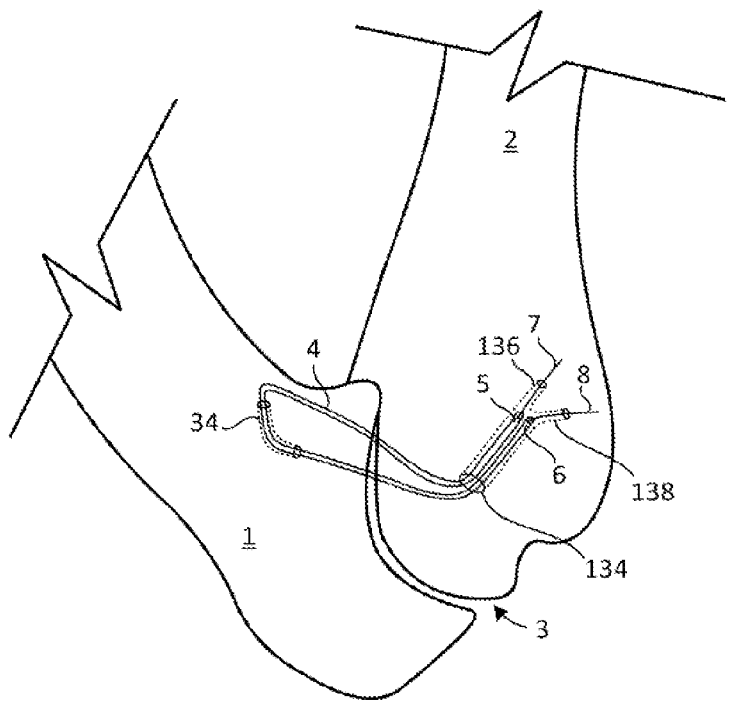
FIG. 8 is a perspective view of the tendon graft placed in the holes formed in the ulna and humerus using the apparatus and method of the present invention.

Referring to FIG. 8, there is shown the tendon graft 4 as placed in the holes of the ulna 1 and humerus 2 of the elbow 3. At this point, the second jig 110 has been removed from the humerus 2, the first end 5 of the tendon graft 4 and the second end 6 of the tendon graft 4 are within the oval tunnel hole 134 in the humerus 2, and the first suture 7 and the second suture 8, which are attached to the first and second ends 5 and 6 of the tendon graft 4, extend outwardly of the first branch hole 136 and the second branch hole 138, respectively. The tendon graft 4 is affixed within the tunnel 134 by first placing a locking plug (not shown) onto the first suture 7, through the first branch hole 136 and into interference-fit relationship with the first end 5 of the tendon graft 4 within the tunnel hole 134. Another locking plug (not shown) is placed on the second suture 8 of the second end 6 of the tendon graft 4 where it travels along the suture 8, through the second branch hole 138, and into interference relationship with the second end 6 of the tendon graft 4 within the oval tunnel hole 134. An interference tendon screw (not shown) is placed at the end of the oval tunnel closest to the joint line of the elbow 3. The locking plugs and the interference tendon screw act to fix the tendon graft 4 to the humerus 2.

It is important to remember that the preferred embodiment of the present invention, as discussed above, applies to the reconstruction of the medial collateral ligament of the elbow. It is intended that the same ligament reconstruction system can be adapted for lateral collateral ligament reconstruction of the elbow. Further, the system present invention is intended to apply to any joint—not just an elbow. The concept of a first jig and a second jig for drilling holes into bones of a joint is equally applicable to a knee, an ankle, a hip, a shoulder and other joints of a body. Naturally, the jigs of a ligament reconstruction of another joint would be formed specially to contour the bones of that joint.

The first plurality of drill guide holes in the method of the present invention are equivalent to the plurality of openings of the first jig 10.

The foregoing disclosure and description of the invention is illustrative and explanatory thereof. Various changes in the details of the illustrated construction can be made within the scope of the appended claims without departing from the true spirit of the invention. The present invention should only be limited by the following claims and their legal equivalents.

I claim:

1. A method for reconstructing a ligament of a joint comprising:
   placing a first jig having a first plurality of drill guide holes on a first bone of the joint;
   forming two intersecting holes in said first bone using said first plurality of drill guide holes of said first jig;
   placing a second jig having a second plurality of drill guide holes on a second bone of the joint;
   forming a tunnel and a first branch hole and a second branch hole in said second bone using said second plurality of drill guide holes, said first branch hole and said second branch hole communicating with said tunnel;
   placing a tendon through a passageway formed by said two intersecting holes in said first bone such that a first end and a second end of said tendon extend outwardly of said passageway;
   attaching a first suture and a second suture to said first and second ends of said tendon, respectively;
   extending said first and second sutures through said tunnel and respectively through said first and second branch holes such that said first and second ends of said tendon are positioned within said tunnel and said first and second sutures extend outwardly respectively of said first and second branch holes; and
   affixing said first and second ends of said tendon within said tunnel.

2. The method of claim 1, further comprising:
   securing said first jig to said first bone prior to the step of forming two intersecting holes;
   securing said second jig to said second bone prior to the step of forming said tunnel and said first branch hole and said second branch hole;
   removing said first jig from said first bone after the step of forming two intersecting holes; and
   removing said second jig from said second bone after the step of affixing said tendon.

3. The method of claim 2, further comprising:
   adjusting a length of said tendon comprising:
      securing said first suture to said second jig;
      clamping said second suture to a handle affixed to said second jig;
      adjusting said first bone and said second bone of the joint to a desired position; and
      adjusting said handle so as to fix said length of said tendon.

4. The method of claim 2, said first bone being an ulna, said second bone being a humerus.

5. The method of claim 2, said step of securing said first jig comprising:
   inserting a first securing pin through a pin guide hole into said first bone adjacent to a joint line; and
   inserting a second securing pin through a cannulated handle removably affixed to said first body into said first bone.

6. The method of claim 5, said step of clamping including pulling said second suture end through a slot in said handle, said slot being centered at a proximal end of said tunnel.

7. The method of claim 1, said step of forming two intersecting holes comprising:

attaching drill sleeves to each of said first plurality of drill guide holes, said drill sleeves having axes intersecting a short distance from said first jig inside said first bone;

inserting a drill bit into each of said drill sleeves;

drilling said intersecting holes with said drill bit in said first bone; and reaming said intersecting holes.

8. The method of claim 1, said step of forming a tunnel comprising:

attaching a first drill guide to a first drill guide hole of said second plurality of drill guide holes;

inserting a drill bit into said first drill guide; and drilling said tunnel to a desired depth.

9. The method of claim 1, said step of forming said first and second branch holes comprising:

attaching a second drill guide to a second drill guide hole of said second plurality of drill guide holes;

inserting a drill bit into said second drill guide;

drilling said first branch hole;

removing said second drill guide from said second drill guide hole;

attaching a third drill guide to a third drill guide hole of said second plurality of drill guide holes;

inserting said drill bit into said third drill guide;

drilling said second branch hole; and removing said third drill guide from said third drill guide hole.

10. The method of claim 9, said first and second branch holes having a smaller diameter than a diameter of said tunnel.

11. The method of claim 1, said step of affixing said first and second ends of said tendon including tying said first and second sutures together.

12. The method of claim 1, said step of affixing said first and second ends of said tendon including placing locking plugs in said tunnel through said first and second branch holes.

13. An apparatus for ligament reconstruction comprising:

a first jig having a body formed so as to fit over a first bone of a joint;

a plurality of openings formed in said body of said first jig, said plurality of openings located on said body so as to have axes intersecting at a desired distance from one side of said first jig;

at least one pin guide hole formed in said body of said first jig;

a handle placed on said body of said first jig;

a second jig arranged in spaced relation to said first jig having a body formed so as to fit over a second bone of said joint;

a first drill guide hole formed in said body of said second jig;

a second drill guide hole and a third drill guide hole formed in said body having axes intersecting at a desired distance from one side of said second jig, said axes intersecting adjacent a longitudinal axis of said first drill guide hole;

at least one fixing hole formed in said body of said second jig; and a second handle affixed on said body of said second jig, said plurality of openings having a diameter of between 10 and 15 millimeters, said first drill guide hole having a diameter of approximately 8 millimeters, said second and third drill guide holes each having a diameter smaller than said diameter of said first drill guide hole.

14. The apparatus of claim 13, said first jig having a surface formed so as to fit over a portion of an ulna of an elbow, said second jig having a surface formed so as to fit over a portion of a humerus of an elbow.

15. An apparatus for ligament reconstruction comprising:

a first jig having a body formed so as to fit over a first bone of a joint;

a first drill guide hole formed in said body of said first jig;

a second and a third drill guide holes formed in said body having axes intersecting at a desired distance from one side of said first jig, said axes intersecting a longitudinal axis of said first drill guide hole;

at least one fixing hole formed in said body of said first jig;

a handle affixed on said body of said first jig;

a second jig arranged in spaced relation to said first jig having a body formed so as to fit over a second bone of said joint;

a plurality of openings formed in said body of said second jig, said plurality of openings located on said body of said second jig so as to have axes intersecting at a desired distance from one side of said second jig;

at least one pin guide hole formed in said body of said second jig; and a second handle placed on said body of said second jig, said first jig having a surface formed so as to fit over a portion of a humerus of an elbow, said second jig having a surface formed so as to fit over a portion of an ulna of an elbow, said plurality of openings having a diameter of between 10 and 15 millimeters, said first drill guide hole having a diameter of approximately 8 millimeters, said second and third drill guide holes having a diameter smaller than said diameter of said first drill guide hole.

* * * * *